(12) United States Patent
Wouters et al.

(10) Patent No.: US 7,288,247 B2
(45) Date of Patent: Oct. 30, 2007

(54) ANTIBODIES FOR USE IN TARGETED AND TEMPORARY TREATMENT OF HUMANS AND ANIMALS

(76) Inventors: Stanislaus Laurens Johan Wouters, Mathidastraat 14, Oosterhout (NL) 4901 HC; Heinz Helmut Renggli, Droogsestraat 2, Malden (NL) 6581 KH; Danielle Angelique Horbach, Bloesemstraat 13, Utrecht (NL) 3581 XA (*) Notice: Subject to any disclaimer, the term of this patent is extended or adjusted under 35 U.S.C. 154(b) by 559 days.

(21) Appl. No.: 09/780,205

(22) Filed: Feb. 9, 2001

(65) Prior Publication Data

US 2002/0034508 A1    Mar. 21, 2002

Related U.S. Application Data

(63) Continuation of application No. PCT/NL99/00509, filed on Aug. 10, 1999.

(30) Foreign Application Priority Data

Aug. 10, 1998 (NL) .................................... 1009834

(51) Int. Cl.
*A61K 39/395* (2006.01)
*A61K 39/00* (2006.01)
*C07K 16/00* (2006.01)

(52) U.S. Cl. ............... 424/130.1; 424/141.1; 424/178.1; 530/387.1; 530/389.1

(58) Field of Classification Search ............. 530/387.1, 530/389.1; 424/130.1, 141.1, 178.1
See application file for complete search history.

(56) References Cited

U.S. PATENT DOCUMENTS

| 4,138,476 A | 2/1979 | Simonson et al. |
| 5,490,988 A | 2/1996 | Beggs et al. |
| 5,571,511 A * | 11/1996 | Fischer |

FOREIGN PATENT DOCUMENTS

| EP | 0 453 097 A2 | 10/1991 |
| EP | 0 736 544 A1 | 10/1996 |
| WO | WO 87/03205 | 6/1987 |
| WO | WO 00/09164 | 2/2000 |

OTHER PUBLICATIONS

Goding ed., Monoclonal Antibodies: Principles and Practice, 1983, pp. 44-45 Academic Press, New York.*
Cole et al., Immunol. &Infect. Diseases 1993, 3, 33-35.*
Weir ed. Immunochemistry, vol. 1, 1986, p. 38 1-38 15 Blackwell Scientific Publication, Oxford.*
PCT International Preliminary Examination Report, PCT/NL99/00509, dated Nov. 15, 2000, 7 pages.
PCT International Search Report, PCT/NL99/00509, dated Nov. 29, 1999, 4 pages.
Abstract, XP-002094889, Oosterwaal et al., "Clearance of a topically applied fluorescein gel from periodontal pockets", *J. Clin. Periodontal*, 17(9) 1 page, Oct. 1990.
PCT International Preliminary Examination Report with amended claims, PCT/NL99/00509, dated Nov. 15, 2000, 12 pages.

* cited by examiner

*Primary Examiner*—Michail Belyavskyi
(74) *Attorney, Agent, or Firm*—TraskBritt

(57) ABSTRACT

An antibody or an antibody fragment that binds to an epitope under specifically chosen conditions; the binding of which to the epitope is broken under specifically chosen different conditions. Also, an antibody or antibody fragment with which a diagnostically, therapeutically or cosmetically active substance is optionally conjugated, for targeted and temporary diagnostic, therapeutic, or cosmetic treatment of externally accessible parts of the human and animal body. Both the specifically chosen binding conditions and the conditions wherein the binding is broken lie within physiologically acceptable limits and involve pH and/or ionic strength. The antibody or antibody fragment can be used for targeted and temporary treatment of externally accessible parts of the human and animal body. Also, a composition including at least one antibody, or a fragment thereof, according to the invention such as a teeth cleaning agent, mouthwash, mouth spray, chewing tablet, cream or ointment.

25 Claims, 12 Drawing Sheets

ANTIBODIES FOR USE IN TARGETED AND TEMPORARY TREATMENT OF HUMANS AND ANIMALS

CROSS REFERENCE TO RELATED APPLICATIONS

Figure 1A:
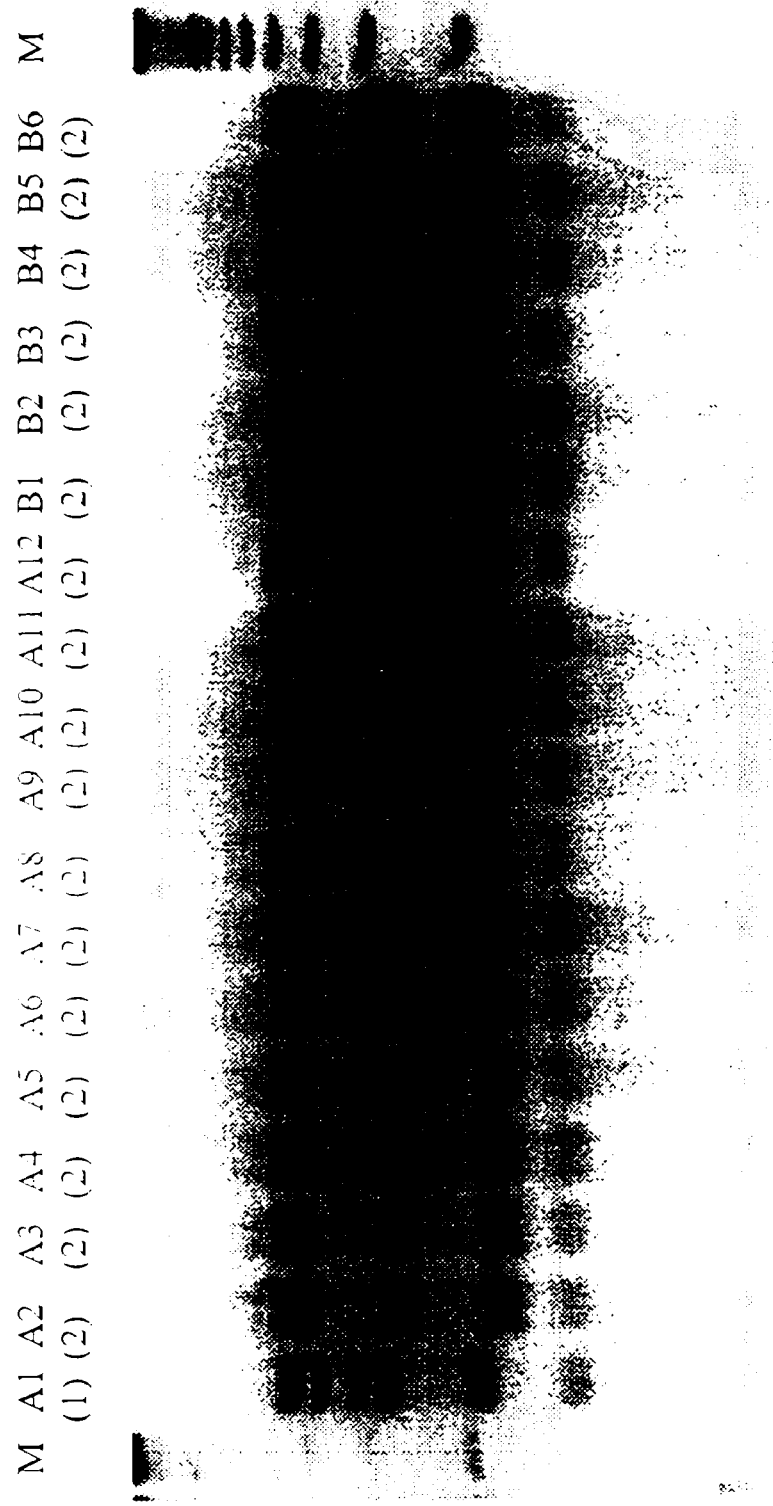

This application claims priority to, and is a continuation of, International Application No. PCT/NL99/00509, filed on Aug. 10, 1999, designating the United States of America, the contents of which are incorporated by this reference, the PCT International Patent Application itself claiming priority from the Netherlands Application Serial No. 1009834, filed Aug. 10, 1998.

The invention relates to antibodies or fragments thereof which can be used for "targeting" of (diagnostically, therapeutically and cosmetically) active substances to desired epitopes. The invention further relates to the use of these antibodies or fragments thereof in the targeted and temporary diagnostic, therapeutic and cosmetic treatment of externally accessible parts of the human and animal body.

The use of an antibody-antigen binding to localize for instance a therapeutically or diagnostically active substance on a determined epitope at a specific site of the body is already known per se. Described for instance in U.S. Pat. No. 5,490,988 and WO 95/01155 are antibodies and fragments of antibodies to which a therapeutically active substance is coupled for the "targeting" of antimicrobial substances to epitopes of pathogenic compounds in the oral cavity. In EP 0736544 are described antibodies which recognize specific protein structures on the tooth. whereby therapeutic or cosmetic substances can be applied specifically and locally to the tooth Targeted and local administering of active substances achieves maximum effectiveness of these substances.

Through conjugation with a dye (for instance erythrocin) such antibodies or fragments thereof can be used for the detection of for instance dental plaque. Early detection of plaque provides the possibility of removing the plaque before it causes infectious or carious disorders of the teeth and/or surrounding tissues. By bringing the teeth and surrounding tissues into contact with the antibody coupled to a dye which detects the plaque, the plaque can be made visible and then be removed by cleaning the teeth and the surrounding tissues, in particular at those locations where the presence of plaque has been determined.

A drawback of the use of antibodies or fragments thereof for detecting dental plaque via this method is the fact that the antibody/epitope binding is not easily broken, whereby dyes visible to the eye remain visible for a longer time. This can be avoided by using dyes based on fluoresceine which are only visible during irradiation with UV-light. These agents are however rather time-consuming in use and not easy for the consumer to use.

The therapeutic treatment of infections in the oral cavity with for instance systemic antibiotics has the important drawback that the antibiotic spreads through the entire body and also reaches other organs and tissues, whereby the natural microbial flora of for instance the gastrointestinal tract can be disrupted. The use of antibiotic gel in the oral cavity may partially prevent this, but has the drawback that it does not remain properly adhered.

It is the object of the invention to obviate the above stated drawbacks. This is achieved by the invention by providing antibodies or fragments thereof which bind to an epitope under specifically chosen conditions, and which elute from that epitope under specifically chosen different conditions. By changing the conditions such that the binding between epitope and antibody is broken, the antibodies can be removed at any desired moment. In this way an infection in for instance the oral cavity can be treated very locally and in targeted manner, and antibodies which are coupled to a dye and which are used for the detection of dental plaque or other oral pathogens can be removed at any desired moment, without lips, tongue and gums remaining coloured for a long time.

An antibody according to the invention is selected using the per se known 'phage-display' technique. Phage-display is a technique for making human antibodies or antibody fragments which can serve for diagnostic or therapeutic purposes and/or for use in research. The phage-display technique makes use of the possibility of expressing proteins in the coat of bacteriophages. In this technique bacteriophages are transfected with human variable (V) genes or with a combination of human variable and constant genes which form the basis for the composition of human antibodies. By ensuring that the synthesized antibodies are expressed as fusion proteins with a bacteriophagous coat protein (for instance g3p), g3p-antibody fusion proteins appear after synthesis on the surface of the bacteriophage.

There are large so-called phage libraries (or banks) of Fab fragments or of single chain Fv fragments (scFv) with different antibody specificities. Such phage libraries are used in the present invention to select the antibody fragments with the specific property that these antibody fragments bind to a determined epitope under specifically chosen conditions and that the binding between antibody fragment and epitope is broken in specifically chosen different conditions.

These specifically chosen conditions can for instance be formed by the pH or the ion strength. For application in the treatment of the human and animal body these conditions preferably lie within physiologically acceptable limits. For use in the oral cavity the pH can for instance be varied between 4 and 8.5 and the ion strength between 0 and 13 M.

Using a selection procedure as described in Example 1, monoclonal phage-antibody fragments (Fab) are obtained with the properties desired for the application such as affinity, specificity and pH and/or ion strength sensitivity. By optionally changing the expression system it is ultimately possible to bring about that Fab fragments or even intact human monoclonal antibodies are secreted into the culture medium. These antibody fragments or intact antibodies can then be isolated easily from the culture medium.

"Fragments" are understood to mean F(ab), F(ab)', F(ab)'$_2$ or scFv fragments.

Diagnostically, therapeutically or cosmetically active substances can be coupled to the obtained antibodies or fragments as is described in EP 0453097, EP 0451972 and EP 0450800, or as according to Lal et al. (Immunol. Meth. 1985; 79:307-318).

Such substances can for instance be enzymes, dyes, fluorescent substances, radioactive substances or antimicrobial compounds. Enzymes can be used as antimicrobial agents (therapeutic), or as a bleaching agent for removing deposits on the teeth (cosmetic treatment). Dyes can be used to detect for instance dental plaque or other oral pathogenic micro-organisms (diagnostic). Antimicrobial compounds can be used to treat infections in the oral cavity or other externally accessible parts of the body.

Antibodies or fragments thereof according to the invention can be used for the treatment of externally accessible parts of the human body, such as the oral cavity, but also the skin and the gastro-intestinal and urogenital system.

An example of an application of antibodies according to the invention is bringing antimicrobial compounds into contact with species of the oral microflora. The oral microflora contains a wide diversity of microbial species including the pathogens: *Actinomyces actinomycetem comitans, Porphyromonas gingivalis, Prevotella intermedia, Streptococcus mutans, Bacteroides forsythus, Eikenella corrodens, Treponema denticola, Campylobacter lectus, Fusobacterium nucleatum*. A number of these species makes a significant contribution toward the forming of plaque. By coupling antimicrobial substances to antibodies or fragments thereof which are targeted against epitopes on these pathogenic compounds, these species can be "attacked" very locally and in targeted manner. As antimicrobial compound can for instance be used an enzyme such as an oxidase (for instance glucose oxidase, lactase oxidase or uric acid oxidase), a peroxidase (for instance horseradish peroxidase, myeloperoxidase, lactoperoxidase or chloroperoxidase), a protease (for instance papain, pepsin, trypsin, ficin or bromelin), a cell wall-lysing enzyme (for instance lysozyme), or a plaque matrix inhibitor (for instance dextranase or mutanase).

The invention further relates to the use of such antibodies or antibody fragments for the manufacture of a medication for targeted and temporary diagnostic, therapeutic and cosmetic treatment of externally accessible parts of the human and animal body. A medication comprising the antibodies or fragments thereof according to the invention can take a number of forms, depending on the area of the body where the medication has to be applied. For application in the oral cavity the medication can for instance take the form of a mouthwash, a lozenge or chewing tablet, a teeth cleaning agent, cream, ointment or chewing gum.

The invention is further illustrated using the annexed examples and figures. Example 1 describes the selection of antibodies and fragments thereof, wherein a Fab-phage library is used as the starting point. A Fab-phage library can for instance be made as described in Marks et al. (J. Mol. Biol. 222: 581-597, 1991) and as described in Haard et al. (J. Biol. Chem. 274:18218-18230, 1999). The annexed examples and figures serve only for the purpose of illustration and are in no way limiting for the invention.

Figure 1B:
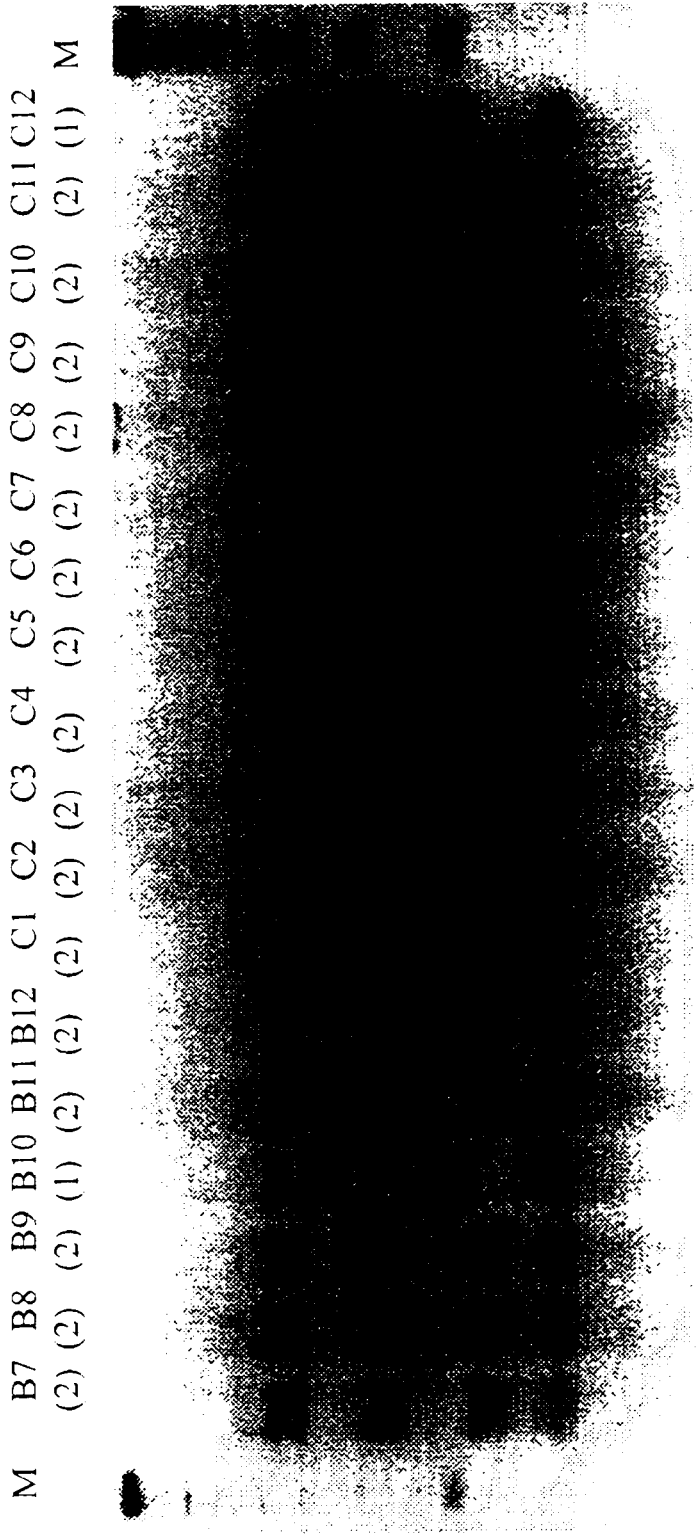
Figure 1C:
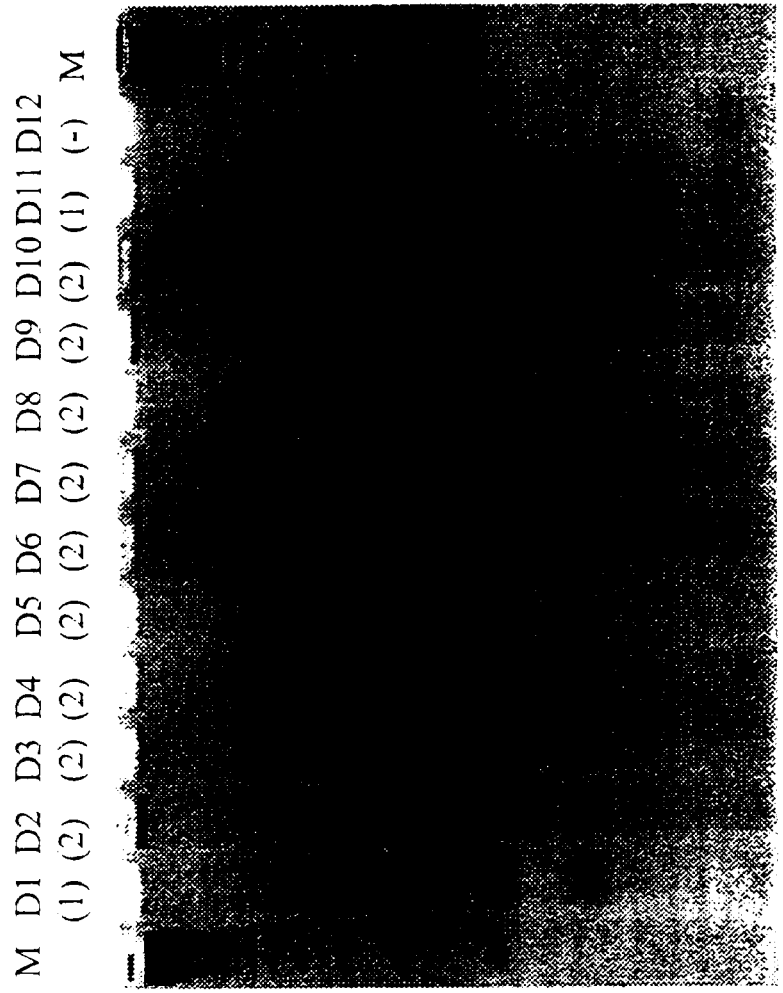
Figure 2A:
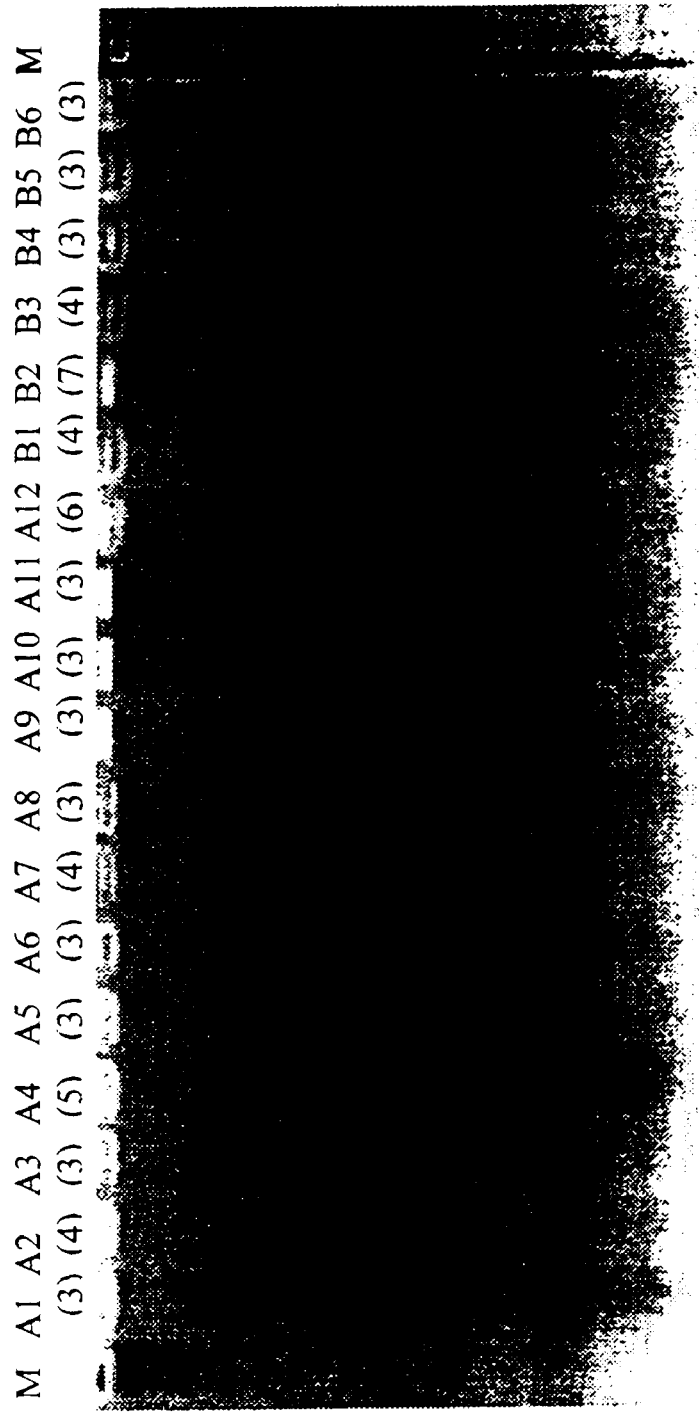
Figure 2B:
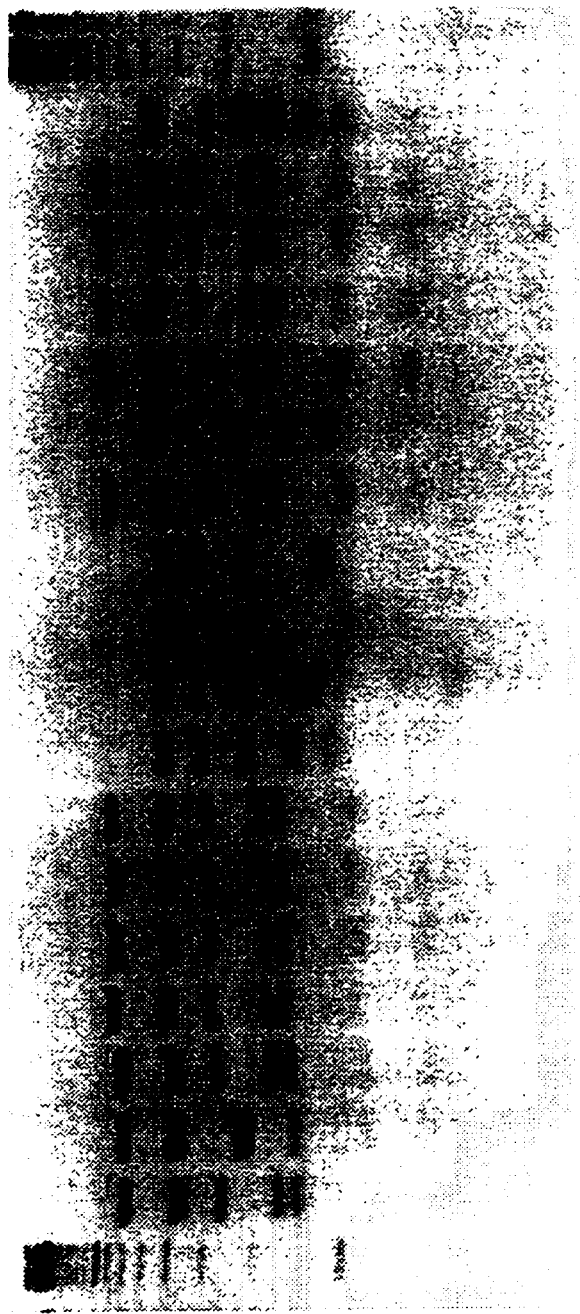
Figure 2C:
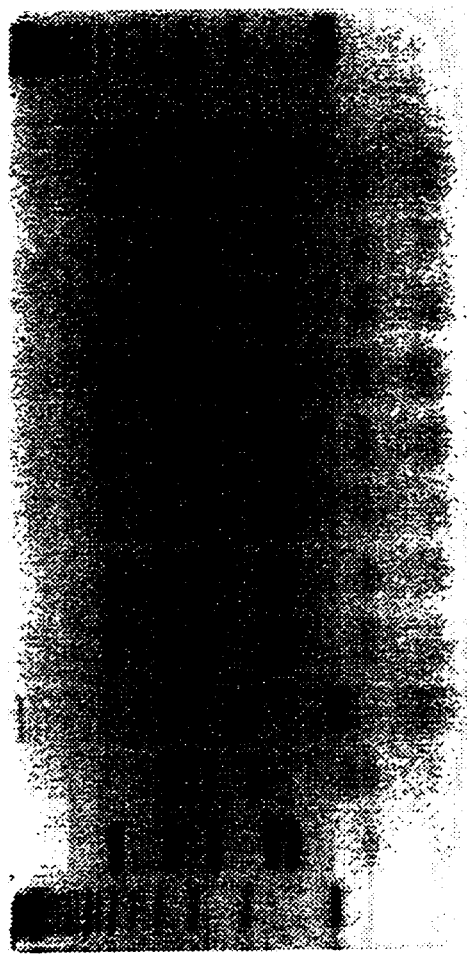
Figure 3A:
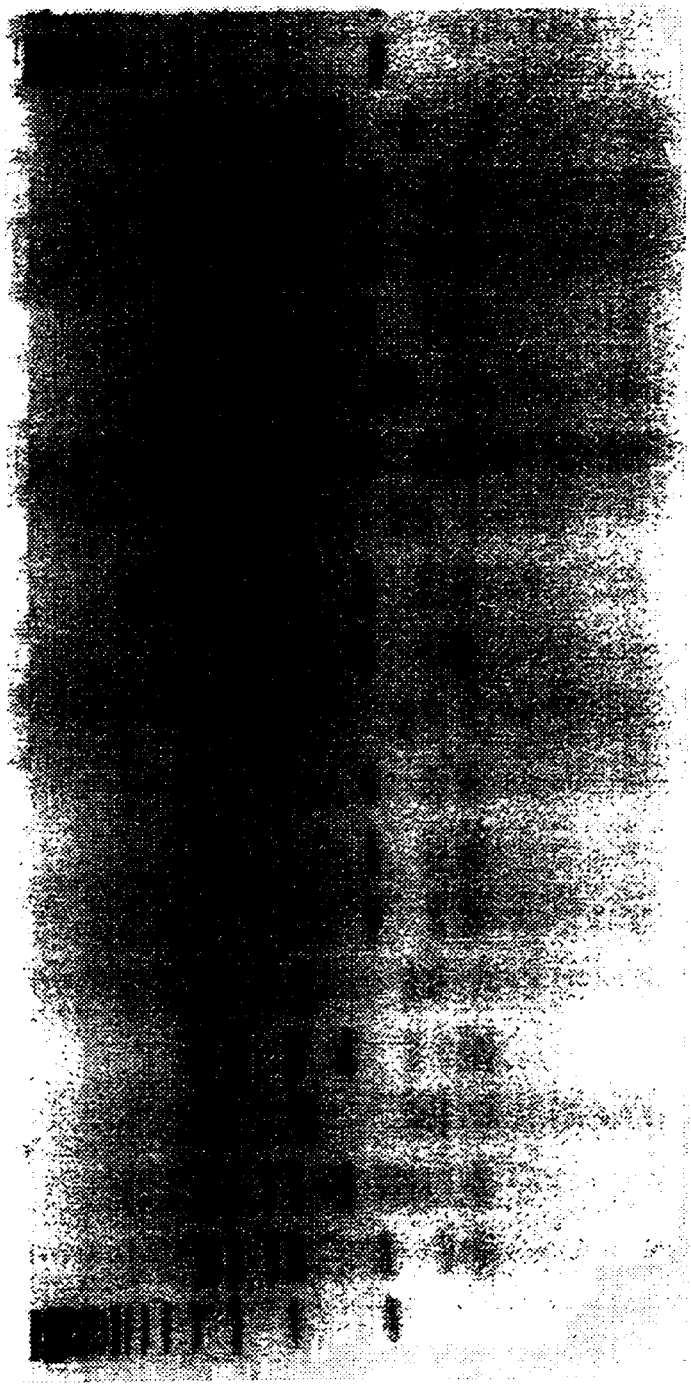
Figure 3B:
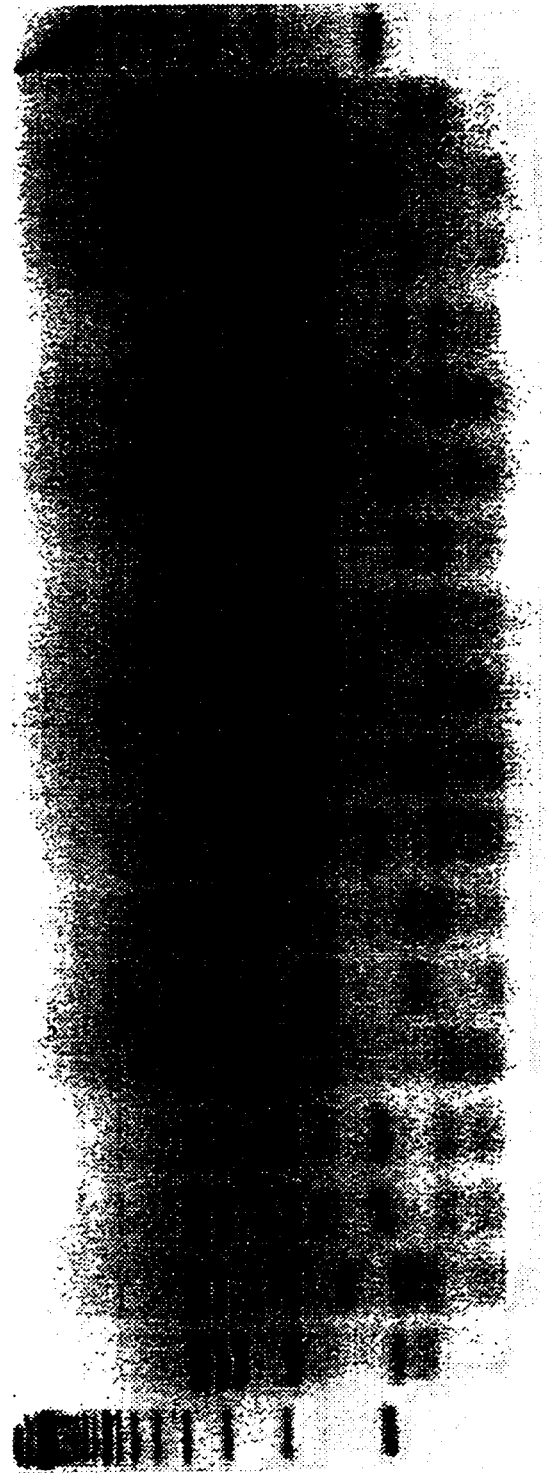
Figure 3C:
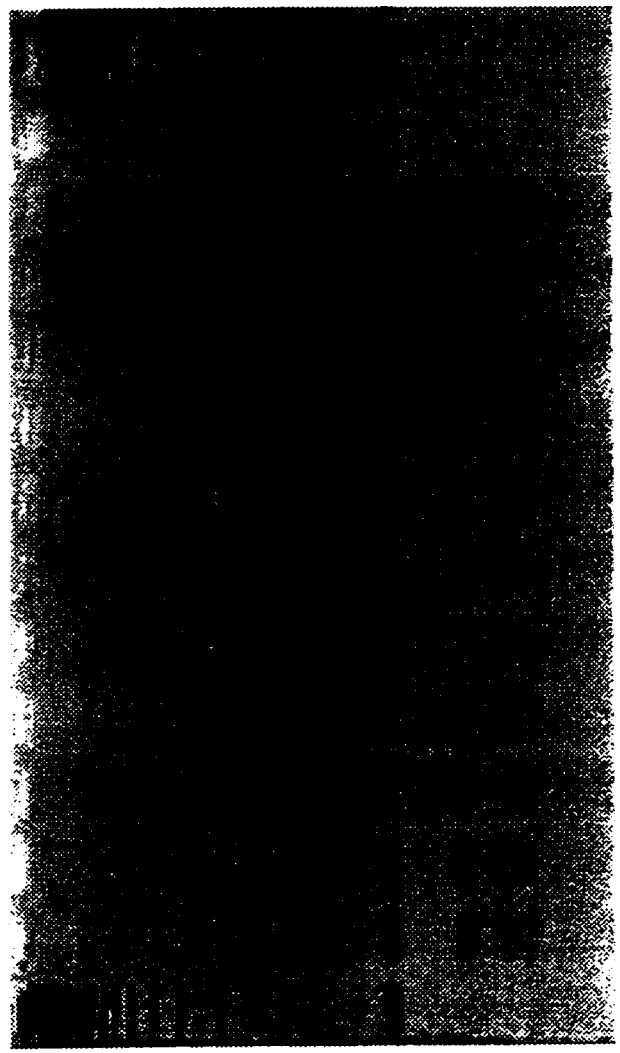
Figure 4A:
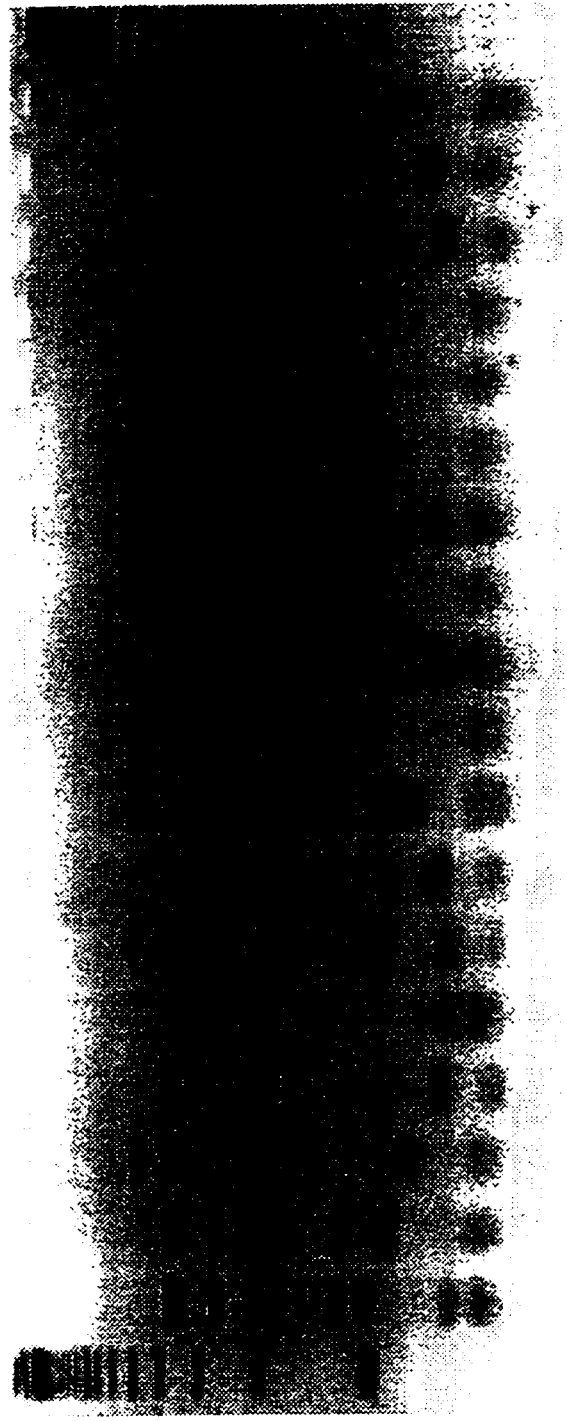
Figure 4B:
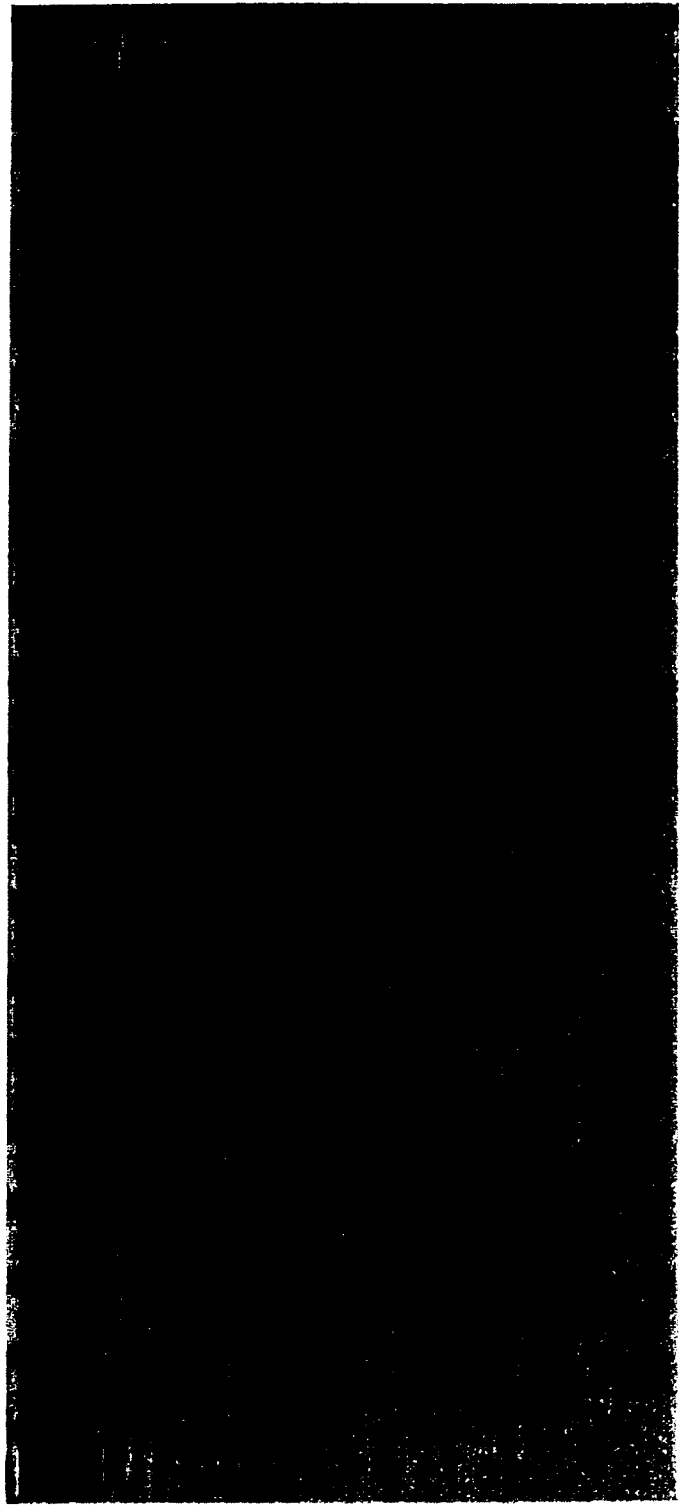
Figure 4C:
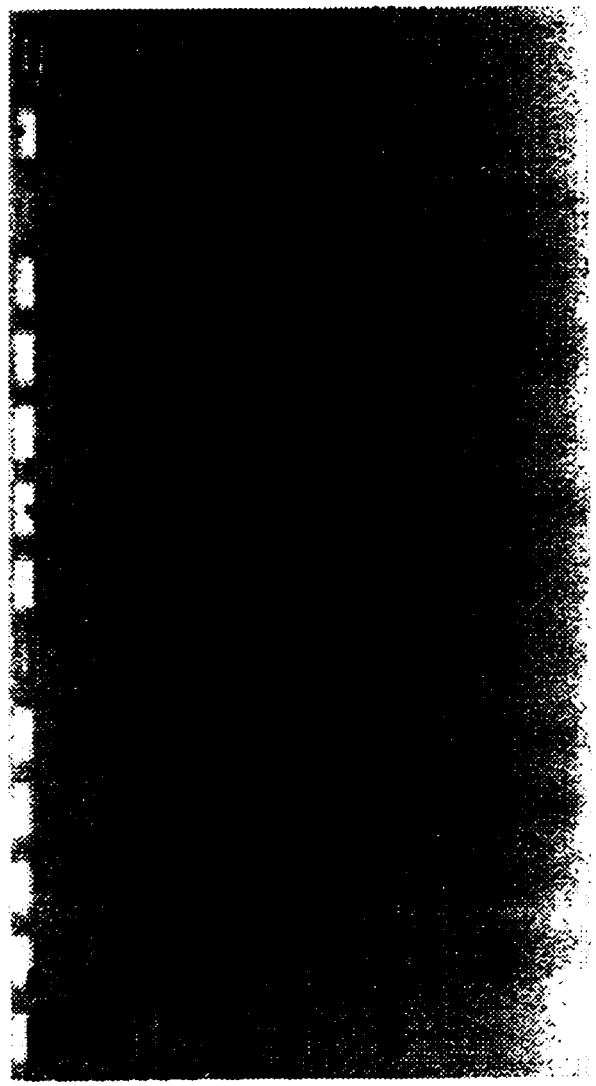

FIGS. 1-4 show the DNA patterns of different clones from respective selection procedures A, B, C and D. For this purpose DNA from the clones from the different selection procedures was replicated using PCR, cleaved with restriction-enzyme BstN-1 and subsequently analysed on 3% agarose gel.

EXAMPLES

Example 1

Selection of Antibodies

The monoclonal antibodies which recognize a specific epitope on the bacterium *Staphylococcus epidermidis* (*S.epidermidis*) and which bind reversibly under conditions which can be used in the oral cavity were obtained using a human Fab phage library.

1.1 Production of Phage Particles from a Library of Antibodies Cloned in Phagemids in *E. coli*

The *E. coli* bacteria were cultured to an $OD_{600nm}$ of 0.5 (=$2*10^9$ bacteria) and helper phages were then added to bring about the formation of phage particles. The infected bacteria were centrifuged and resuspended in culture buffer. After an overnight culture the bacteria were removed using centrifugation, and the phages were precipitated out of the culture medium by means of PEG precipitation. The precipitated phages were resuspended in one of the four binding buffers of table 1, and were subsequently used in the different selection procedures.

1.2 Selection of the Phages $1*10^9$ bacteria (*S.epidermidis*) (in the different binding buffers, see table 1) were incubated with phages (input) (see 1.1). The bacteria were then washed 12 times with binding buffer and the phages that had bound were eluted with the correct elution buffer (see table 1). After elution 55% of the bacteria was still alive.

The eluted phages were replicated via infection of *E. coli*, followed by culture of the infected *E. coli* as according to 1.1. The cultured eluted phages were then reused in the following selection round (input). The described selection procedures were carried out 4 times.

TABLE 1

| Selection | Binding buffer | Elution buffer |
|---|---|---|
| A | PBS (pH 7.4) | pH 4.5 |
| B | PBS (pH 7.4) | pH 4.5 + 1 M NaCl |
| C | pH 8.5 + 1 M NaCl | Milli Q |
| D | pH 8.5 | pH 4.5 + 1 M NaCl |

Table 2 shows the titration results of the different selection procedures on *S.epidermidis*. These results demonstrate that for selection procedure B and C the number of specific phages does not increase any further after three selection rounds. In addition, the fact that in selection B, C, and D the titer of the final washing step is lower than the titer of the eluted fraction (output) shows that specific elution has occurred. In selection A this is not the case and there is therefore probably no specific elution in this case. The increasing Output/Input ratio shows the enrichment of binding and eluting phages after the different selection rounds.

1.3 Screening Using "Whole Cell" ELISA 188 clones (24 clones from round 3 and 23 clones from round 4 of selection A and D, and 42 clones from round 3 and 5 clones from round 4 of selection B and C) were selected at random and tested as phage-antibodies in the Whole Cell ELISA in a 96-well plate as described below, for screening for antibodies which bind specifically to *S.epidermidis*.

TABLE 2

| Selection | Round | Input[1] | Titer[2] | Output[3] | Output/Input |
|---|---|---|---|---|---|
| A | 1 | $6.9*10^{12}$ | — | $7.5*10^4$ | $1.1*10^{-8}$ |
|   | 2 | $7.4*10^{13}$ | — | $1.7*10^5$ | $2.3*10^{-9}$ |
|   | 3 | $1.8*10^{13}$ | $1.1*10^8$ | $1.3*10^7$ | $7.2*10^{-7}$ |
|   | 4 | $2.5*10^{13}$ | $8.8*10^8$ | $2.0*10^8$ | $8.0*10^{-6}$ |
| B | 1 | $5.4*10^{12}$ | — | $5.8*10^5$ | $1.1*10^{-7}$ |
|   | 2 | $8.3*10^{13}$ | — | $6.6*10^7$ | $8.0*10^{-7}$ |
|   | 3 | $8.3*10^{12}$ | $5.5*10^9$ | $3.4*10^{10}$ | $4.1*10^{-3}$ |
|   | 4 | $5.8*10^{12}$ | $6.5*10^9$ | $3.9*10^{10}$ | $6.7*10^{-3}$ |
| C | 1 | $6.0*10^{12}$ | — | $1.2*10^6$ | $2.0*10^{-7}$ |
|   | 2 | $2.7*10^{13}$ | — | $2.0*10^7$ | $7.4*10^{-7}$ |
|   | 3 | $1.1*10^{13}$ | $3.1*10^9$ | $3.4*10^{10}$ | $3.1*10^{-3}$ |
|   | 4 | $4.7*10^{12}$ | $2.1*10^9$ | $3.1*10^{10}$ | $6.6*10^{-3}$ |
| D | 1 | $6.5*10^{12}$ | — | $1.9*10^7$ | $2.9*10^{-6}$ |
|   | 2 | $3.6*10^{13}$ | — | $1.1*10^8$ | $3.1*10^{-6}$ |
|   | 3 | $1.9*10^{13}$ | $1.7*10^8$ | $5.0*10^9$ | $2.6*10^{-4}$ |
|   | 4 | $9.3*10^{12}$ | $4.9*10^8$ | $1.1*10^{10}$ | $1.2*10^{-3}$ |

[1]Input (total cfu) (cfu = colony forming unit)
[2]Titer (total cfu of the final washing step before elution)
[3]Output (total cfu)

Monoclonal phage particles (individual clones) were incubated with *S.epidermidis* ($2*10^7$ bacteria per well) in binding buffer in a 96-well plate. The bacteria were then washed thoroughly with binding buffer (by means of centrifuging followed by resuspension), whereafter the phage particles were eluted with elution buffer (or binding buffer as control) for 30 minutes. After the elution the bacteria were centrifuged and the presence of phage particles on the bacteria was demonstrated by means of peroxidase-labelled mouse-anti-M13 antibodies and 3,3',5,5'-tetramethylbenzidine (TMB). The plate was measured at 405 nm. In the Whole Cell ELISA the same combinations of binding and elution buffers were used as during the selection.

Clones with an ELISA signal which was twice as high as the background signal when elution took place with the binding buffer (control) were designated "positive clones". Positive clones are therefore all clones which bind specifically to the bacterium at the chosen binding condition, irrespective of the fact of whether they elute in other conditions. Clones with an ELISA signal after elution with binding buffer which was twice as high as the ELISA signal after elution with elution buffer were designated "specifically eluting clones". The specifically eluting clones are therefore the antibody-phage clones which bind in the binding buffer used, and which do not elute in the binding buffer but do so when washed with the elution buffer. The specifically eluting clones therefore bind under specifically chosen conditions and elute under specifically chosen different conditions. Table 3 shows the results of the Whole Cell ELISA.

The fact that in the group of clones from selection A not a single specifically eluting clone was found confirms the supposition that in selection A specific elution did not occur (see 1.2).

TABLE 3

| Selection | number of positive clones | number of specifically eluting clones |
|---|---|---|
| A | 47/47 | 0/47 |
| B | 47/47 | 30/47 |
| C | 47/47 | 7/47 |
| D | 25/47 | 13/47 |

1.4 "Fingerprint Analysis" of the Positive Clones

All 188 clones from the 4 selections were screened with fingerprint analysis as described hereinbelow in order to determine the diversity of the clones. Using the fingerprint analysis DNA patterns were obtained which were subsequently used to distinguish the different clones. The clones were tested for the presence of an insert of 1700 bp (clones which code for Fab must have an insert of about 1700 bp). All tested clones (except 1 clone from selection C, and 8 clones from selection D) contained the specific insert.

For the fingerprint analysis, DNA of the individual clones was replicated using PCR and then cleaved with restriction-enzyme BstN-1. The DNA samples were analysed on 3% agarose gel with 0.5 µg/ml ethidium bromide. Shown in FIGS. 1-4 are the DNA patterns of the individual clones. The clones are numbered in accordance with their position on the ELISA plate. The results show that respectively 2, 12, 13 and 32 different DNA patterns ("fingerprints") are present in selection A, B, C and D. Patterns 4, 5 and 14 occur in both selection B and D. Patterns 10 and 12 are found in both selection B and C. Pattern 24 occurs in selection C and D and pattern 3 is found in selections B, C and D. There are therefore clones which elute due to a pH-shock, and there are other clones which elute due to a salt-shock, or through a combination of pH and salt-shock.

When the results of the Whole Cell ELISA are compared to the results of the DNA patterns (see table 4), there are 16 clones (with different DNA patterns) which are positive in the binding to S.epidermidis and which elute specifically after binding.

TABLE 4

| fingerprint pattern | selection |
|---|---|
| 6, 7, 8, 9, 11, 13 | B |
| 17, 18, 21, 22 | C |
| 47, 51 | D |
| 12 | B, C |
| 5, 14 | B, D |
| 3 | B, C, D |

1.5 Determining the Specificity

The 16 specific clones according to the invention were tested in an ELISA for binding to streptavidin, biotin-labelled BSA, thyroglobulin and to an empty well. None of the 16 clones bound to any of the coated antigens. The binding to S.epidermidis in elution buffer and to S.epidermidis in binding buffer was tested in the Whole Cell ELISA. All 16 clones according to the invention bound only to S.epidermidis in binding buffer and not in elution buffer.

Example 2

Toothpaste

A clone from selection C (Example 1) was used to prepare a toothpaste with phage-antibody fragments coupled to erythrocin for the purpose of demonstrating the presence of S.epidermidis in the oral cavity. The phage-antibody fragments from selection procedure C bind to S.epidermidis at a pH of 8.5 and a salt concentration of 1 M NaCl. The binding of antibody to S.epidermidis is made visible by the bound dye. By then rinsing with water (pH 7) the binding is broken and the bound erythrocin removed.

Example 3

Ion Strength as Specifically Chosen Condition

An ion strength of between about 0 and 13 M can be used in the oral cavity.

In a different embodiment according to the invention the antibody or a fragment thereof having coupled thereto a suitable diagnostically, therapeutically or cosmetically active substance binds at an ion strength of between 0 and 500 mM. The binding is then broken at any desired moment by rinsing with a mouthwash having an ion strength of 1-13 M.

What is claimed is:

1. A selected monoclonal antibody, or fragment thereof, wherein:
   the selected monoclonal antibody, or fragment thereof, has been selected for its ability to bind to an epitope at a first pH of 8.5; and
   the selected monoclonal antibody, or fragment thereof, has also been selected such that the bond of the selected monoclonal antibody, or fragment thereof, to the epitope is broken at a second pH of 7.

2. The selected monoclonal antibody, or fragment thereof, of claim 1, wherein the selected monoclonal antibody, or fragment thereof, is coupled to a diagnostically, therapeutically or cosmetically active substance.

3. The selected monoclonal antibody, or fragment thereof, of claim 1, wherein the ability of the selected monoclonal antibody, or fragment thereof, to bind to the epitope has been further selected dependent upon ion strength.

4. The selected mono clonal antibody, or fragment thereof, of claim 3, wherein:
a first ion strength at which the selected monoclonal antibody binds the epitope is different than a second ion strength at which the bond between the selected monoclonal antibody and the epitope is broken.

5. The selected mono clonal antibody, or fragment thereof, of claim 1, wherein the selected monoclonal antibody, or fragment thereof, is selected from a group consisting of a F(ab), F(ab)', F(ab)'$_2$ and an scFv.

6. The selected monoclonal antibody, or fragment thereof, of claim 1, wherein the selected monoclonal antibody, or fragment thereof, is capable of use in a targeted or temporary diagnostic, therapeutic and cosmetic treatment of externally accessible parts of the human or the animal body.

7. The selected monoclonal antibody, or fragment thereof, of claim 6, wherein said targeted or temporary diagnostic, therapeutic or cosmetic treatment comprises a treatment of an oral cavity of the human or the animal body.

8. The selected monoclonal antibody, or fragment thereof, of claim 7, wherein the selected monoclonal antibody, or fragment thereof, is capable of bleaching teeth and molars included in said oral cavity.

9. The selected monoclonal antibody, or fragment thereof, of claim 7, wherein the selected monoclonal antibody, or fragment thereof, is capable of detecting plaque in said oral cavity.

10. The selected monoclonal antibody, or fragment thereof, of claim 7, wherein the selected monoclonal antibody, or fragment thereof, is capable of removing plaque in said oral cavity.

11. The selected monoclonal antibody, or fragment thereof, of claim 6, wherein said targeted or temporary diagnostic, therapeutic or cosmetic treatment comprises a treatment for fighting infections in externally accessible parts of the human or the animal body.

12. The selected monoclonal antibody, or fragment thereof, of claim 2, wherein the diagnostically, therapeutically or cosmetically active substance comprises an enzyme.

13. The selected monoclonal antibody, or fragment thereof, of claim 12, wherein the enzyme is selected from the group consisting of an oxidase, a peroxidase, a protease, a cell-wall lysing enzyme and a plaque matrix inhibitor.

14. The selected monoclonal antibody, or fragment thereof, of claim 13, wherein the enzyme comprises an oxidase selected from the group consisting of glucose oxidase, lactase oxidase and uric acid oxidase.

15. The selected monoclonal antibody, or fragment thereof, of claim 13, wherein the enzyme comprises the protease and is selected from the group consisting of papain, pepsin, trypsin, ficin and bromelin.

16. The selected monoclonal antibody, or fragment thereof of claim 2, wherein the diagnostically, therapeutically or cosmetically active substance comprises a fluorescent or radioactive substance.

17. The selected monoclonal antibody, or fragment thereof, of claim 2, wherein the selected monoclonal antibody, or fragment thereof, is capable of binding an epitope of a pathogenic micro-organism or other pathogenic compound.

18. The selected monoclonal antibody, or fragment thereof, of claim 17, wherein said pathogenic micro-organism is selected from the group consisting of *Actinomyces actinomycetem comitans, Porphyromonas gingivalis, Prevotella intermedia, Streptococcus mutans, Bacteroides forsythus, Eikenella corrodens, Treponema denticola, Campylobacter lectus*, and *Fusobacterium nucleatum*.

19. A composition comprising:
at least one selected monoclonal antibody, or fragment thereof, of claim 1; and
at least one physiologically acceptable diluent, solvent or carrier.

20. The composition of claim 19, wherein the composition is selected from the group consisting of a teeth cleaning agent, mouthwash, mouth spray, chewing tablet, chewing gum, cream and ointment.

21. The selected monoclonal antibody, or fragment thereof, of claim 4, wherein the first ion strength is 1 M NaCl and the second ion strength is 0 M.

22. A selected monoclonal antibody, or fragment thereof, wherein:
the selected monoclonal antibody, or fragment thereof, has been selected for its ability to bind an epitope at a first pH of 8.5; and
the selected monoclonal antibody, or fragment thereof, has also been selected such that the bond of the selected monoclonal antibody, or fragment thereof, to the epitope is broken at a second pH of 4.5 and an ion strength of 1M NaCi.

23. The selected monoclonal antibody, or fragment thereof, of claim 1, wherein the epitope is of a *Staphylococcus epidermidis* origin.

24. The selected monoclonal antibody, or fragment thereof, of claim 22, wherein the ability of the selected monoclonal antibody, or fragment thereof, to bind to the epitope has been further selected dependent upon ion strength.

25. The selected monoclonal antibody, or fragment thereof, of claim 24, wherein the ion strength is equivalent to about 1M NaCl.

* * * * *